United States Patent [19]

Nishikido et al.

[11] Patent Number: 4,902,793
[45] Date of Patent: Feb. 20, 1990

[54] PROCESS FOR PREPARING 3-ALKOXYMETHYLCEPHALOSPORINS

[75] Inventors: Joji Nishikido, Fuji; Kentaro Fukuzaki, Nobeoka, both of Japan

[73] Assignee: Asahi Kasei Kogyo Kabushiki Kaisha, Japan

[21] Appl. No.: 103,217

[22] Filed: Oct. 1, 1987

[30] Foreign Application Priority Data

| Oct. 2, 1986 | [JP] | Japan | 61-233331 |
| Dec. 4, 1986 | [JP] | Japan | 61-287773 |
| Jul. 27, 1987 | [JP] | Japan | 62-185356 |
| Aug. 24, 1987 | [JP] | Japan | 62-208297 |

[51] Int. Cl.$^4$ .................. C07D 501/04; A61K 31/545
[52] U.S. Cl. .................................... 540/230; 540/215; 540/222
[58] Field of Search ............... 540/215, 222, 226, 227, 540/230

[56] References Cited

U.S. PATENT DOCUMENTS

| 3,658,799 | 4/1972 | Eardley | 260/243 C |
| 3,665,003 | 5/1972 | Kennedy et al. | 260/243 C |
| 3,790,567 | 2/1974 | Kennedy et al. | 260/243 C |
| 3,846,416 | 11/1974 | Kennedy et al. | 260/243 C |
| 3,948,906 | 4/1976 | Eardley | 260/243 C |
| 4,482,710 | 11/1984 | Fujimoto et al. | 540/230 |

FOREIGN PATENT DOCUMENTS 204657 12/1986 European Pat. Off. .
59-163387 9/1984 Japan .

OTHER PUBLICATIONS

J. Med. Chem., vol. 14, p. 113, (1971).

Primary Examiner—Nicholas S. Rizzo
Attorney, Agent, or Firm—Finnegan, Henderson, Farabow, Garrett & Dunner

[57] ABSTRACT

A process for preparing 3-alkoxymethylcephalosporins which are useful as an intermediate for various cephalosporin derivatives having a high antimicrobial activity is disclosed. According to the process of the present invention, the 3-alkoxymethylcephalosporins can be easily obtained in high yield on a commercial scale.

17 Claims, No Drawings

PROCESS FOR PREPARING 3-ALKOXYMETHYLCEPHALOSPORINS

BACKGROUND OF THE INVENTION

1. Field Of The Invention

This invention relates to a process for preparing 3-alkoxymethylcephalosporins which are useful as intermediates for various cephalosporin derivatives having a high antimicrobial activity across a broad antimicrobial spectrum. More particularly, the present invention relates to a process for preparing a 3-alkoxymethyl-3-cephem-4-carboxylic acid represented by the formula (II) or its derivative, or a salt thereof,

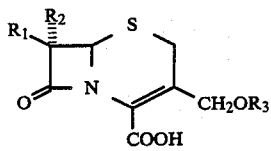

wherein $R_1$ represents an amino group or a protected amino group, $R_2$ represents a hydrogen atom or a lower alkoxy group and $R_3$ represents an unsubstituted or substituted lower alkyl group, which can be easily carried out on a commercial scale and which can give the desired product in high yield.

2. Discussion Of Related Art

As a process for preparing a 3-alkoxymethyl-3-cephem-4-carboxylic acid represented by the formula (II), there have heretofore been proposed, for example, a method (1) in which the corresponding 3-acetoxymethyl compound is reacted with a lower aliphatic alcohol in the absence of a catalyst (see, for example, U.S. Pat. Nos. 3,665,003, 3,790,567 and 3,846,416), a method (2) in which the corresponding 3-hydroxymethyl compound is reacted with an alkylating agent (see, for example, U.S. Pat. Nos. 3,665,003, 3,790,567 and 3,846,416), a method (3) in which the corresponding 3-halomethyl compound is reacted with a lower aliphatic alcohol (see, for example, U.S. Pat. Nos. 3,658,799 and 3,948,906), a method (4) in which the corresponding 3-haloacetoxymethyl compound is reacted with a lower aliphatic alcohol (see, for example, U.S. Pat. Nos. 3,658,799 and 3,948,906), and a method (5) in which the corresponding $\Delta^2$-3-halomethyl compound is reacted with a lower aliphatic alcohol and then subjected to isomerization [see, for example, J. Med. Chem. 14, 113(1971)].

None of the above-mentioned conventional methods (1), (2), (3), (4) and (5) can be satisfactorily practiced on a commercial scale. According to method (1), the yield of the desired product is as low as about 10 %. In method (2), it is disadvantageously necessary not only to protect the carboxyl group at the 4-position, but also to use toxic diazomethane in a large amount. According to method (3), it is also disadvantageously necessary to prepare the 3-halomethyl compound from the corresponding 3-acetoxymethyl compound through two steps and then to protect the carboxyl group at the 4-position and, in addition, the yield of the desired product is low. According to method (4), it is disadvantageously necessary to prepare the 3-haloacetoxymethyl compound from the corresponding 3-acetoxymethyl compound through three to four steps and, in addition, the yield of the desired product is low. Further, according to method (5), there are involved such a sequence of many steps that the starting $\Delta^3$-3-methyl compound is isomerized to the corresponding $\Delta^2$-3-methyl compound, followed by halogenation to obtain the corresponding $\Delta^2$-3-halomethyl compound and, after the reaction of the $\Delta^2$-3-halomethyl compound with a lower aliphatic alcohol, the reaction product is again isomerized to the corresponding 3-cephem compound.

Further, there has also been proposed a method (6) in which the corresponding 3-acetoxymethyl compound is reacted with a lower aliphatic alcohol in the presence of a bromide, iodide or chloride, for example, a metal iodide such as lithium iodide, sodium iodide, magnesium iodide or the like; a quarternary ammonium iodide such as N-methylpyridinium iodide or the like; and a chloride or bromide of an alkali metal, an alkaline earth metal or a quaternary ammonium (see, for example, U.S. Pat. No. 4,482,710 and Japanese Pat. Application Laid-Open Specification No. 57-192392). A method (7) has also been proposed in which the corresponding 3-acetoxymethyl compound (7-aminocephalosporanic acid) is reacted with a lower aliphatic alcohol in the presence of a sulfonic acid or its derivative (Japanese Pat. Application Laid-Open Specification No. 59-163387). A method (8) has been proposed in which the corresponding 3-acetoxymethyl compound (7-aminocephalosporanic acid) is reacted with a lower aliphatic alcohol in the presence of boron trifluoride or a complex of boron trifluoride (European Pat. Application Publication No. 204657). Likewise, methods (6), (7) and (8) are commercially disadvantageous in that the yield of the desired product is low and complicated steps are required for isolating the desired product.

Therefore, there is still a strong demand in the art for an improved process of preparing a 3-alkoxymethyl-3-cephem-4-carboxylic acid.

SUMMARY OF THE INVENTION

The present inventors have made extensive and intensive studies with a view to developing a process for preparing 3-alkoxymethylcephalosporins represented by the formula (II) which can be easily, simply practiced to give the desired products with high purity in high yield. As a result, it has unexpectedly been found that the object can be attained by the use of a specific catalyst.

According to the present invention, there is provided a process for preparing a 3-alkoxymethyl-3-cephem-4-carboxylic acid represented by the formula (II) or its derivative at the carboxyl group, or a salt of said carboxylic acid or said derivative

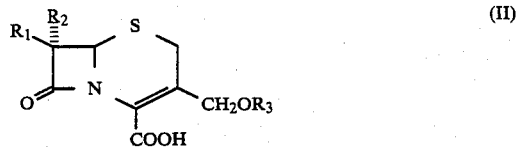

wherein $R_1$ represents an amino group or a protected amino group, $R_2$ represents a hydrogen atom or a lower alkoxy group and $R_3$ represents an unsubstituted or substituted lower alkyl group, which comprises reacting a cephalosporanic acid represented by the formula (I) or its derivative at the carboxyl group, or a salt of said cephalosporanic acid or said derivative

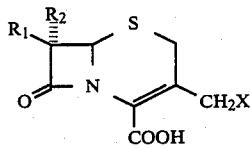

(I)

wherein $R_1$ and $R_2$ have the same meanings as defined above, and X represents an unsubstituted or substituted acyloxy group or an unsubstituted or substituted carbamoyloxy group,
with an alcohol represented by the formula (III):

$$R_3\text{—OH} \tag{III}$$

wherein $R_3$ has the same meaning as defined above,
in the presence of at least one first member selected from the group consisting of halides of antimony, tin, iron, zinc and bismuth and complexes of halides of antimony, tin, iron, zinc and bismuth.

Additional objects and advantages of the invention will be set forth in part in the description which follows, and in part will be obvious from the description, or may be learned by practice of the invention. The objects and advantages of the invention may be realized and obtained by means of instrumentalities and combinations particularly pointed out in the appended claims.

In the above formulae (I) and (II), $R_1$ represents an amino group or a protected amino group. The type of the protecting group of the protected amino group is not limited as long as not only the protecting group does not have an adverse effect on the reaction in the process of the present invention but also the protecting group is not affected during the reaction Exemplary suitable protected amino group include an acylated amino group and a group formed by the condensation of an amino group with an aldehyde (Shiff base). Exemplary suitable acyl groups of the acylated amino group include aliphatic acyl groups such as a formylacetyl group, a propionyl group, a butyryl group, an isobutyryl group, an adipoyl group and an aminoadipoyl group; aromatic acyl groups such as a benzoyl group, a toluoyl group and a phthaloyl group; acyl groups having a heterocyclic ring, such as an oxazolylacetyl group, a thiazolylacetyl group and a thienylacetyl group; and alkoxycarbonyl groups such as an ethoxycarbonyl group, a t-butoxy carbonyl group, a benzyloxycarbonyl group and a trichloroethoxycarbonyl group. The above-mentioned acyl groups may contain substituent groups such as an amino group, a mercapto group, an alkylthio group and a cyano group. The above-mentioned substituent groups may be protected by a customary protecting group which does not have an adverse effect on the reaction in the process of the present invention and is not affected during the reaction. As the group formed by the condensation of the amino group with an aldehyde, there may be mentioned, for example, a salicylideneamino group, a benzylideneamino group and a group formed by the condensation of the amino group with ethyl acetoacetate.

In the above formulae (I) and (II), $R_2$ represents a hydrogen atom or a lower alkoxy group. The term "lower alkoxy group" as used herein means an alkoxy group having 1 to 4 carbon atoms. Exemplary suitable alkoxy groups include methoxy, ethoxy, n-propoxy, isopropoxy and n-butoxy, isobutoxy, sec.-butoxy, tert.-butoxy and the like. Exemplary suitable unsubstituted or substituted acyloxy groups represented by X include alkanoyloxy groups having 1 to 10 carbon atoms such as acetoxy, propionyloxy, butyryloxy and the like. X may also represent an unsubstituted or substituted carbamoyloxy group. As the substituent of the substituted acyloxy group or substituted carbamoyloxy group, there can be mentioned, for example, a halogen atom, a nitro group, a lower alkyl group having 1 to 5 carbon atoms, an alkoxy group having 1 to 5 carbon atoms, an alkylthio group having 1 to 5 carbon atoms, an aliphatic acyloxy group having 1 to 5 carbon atoms, an aromatic acyloxy group having 6 to 10 carbon atoms, an aliphatic acylamino group having 1 to 5 carbon atoms, an aromatic acylamino group having 6 to 10 carbon atoms, a hydroxyl group, carboxyl group, a sulfamoyl group, a carbamoyl group, a carboalkoxycarbamoyl group and the like, which are all known as suitable substituents for an acyloxy or carbamoyloxy group.

Examples of derivatives at the carboxyl group of the cephalosporanic acid represented by the formula (I) include esters, amides, other condensation products and protecting group-protected derivatives.

The suitable esters are those which do not have an adverse effect on the reaction, for example, substituted or unsubstituted alkyl esters such as methyl ester, ethyl ester, propyl ester, isopropyl ester, butyl ester, tert.-butyl ester, methoxymethyl ester, ethoxyethyl ester, phenoxymethyl ester, methylthiomethyl ester, methylthioethyl ester, phenylthiomethyl ester, dimethylaminoethyl ester, diethylaminoethyl ester, morpholinoethyl ester, piperidinoethyl ester, acetylmethyl ester, phenacyl ester, acetoxymethyl ester, pivaloyloxymethyl ester, benzoyloxymethyl ester, methanesulfonylethyl ester, toluenesulfonylethyl ester, bromomethyl ester, iodoethyl ester, trichloroethyl ester and phthal imidomethyl ester; cycloalkyl esters such as cyclohexyl ester and cycloheptyl ester; substituted or unsubstituted aryl esters such as phenyl ester, tolyl ester, xylyl ester, naphthyl ester, p-nitrophenyl ester, 2,4-dinitrophenyl ester, p-methoxyphenyl ester, trichlorophenyl ester and p-methanesulfonyl ester; substituted or unsubstituted aralkyl ester such as benzyl ester, phenethyl ester p-chlorobenzyl ester, p-nitrobenzyl ester, p-methoxybenzyl ester, diphenylmethyl ester and trityl ester; indanyl ester; and phthalidyl ester.

Exemplary suitable amides include acid amides, N-monosubstituted acid amides and N-disubstituted acid amides such as N-alkyl acid amides for example, N-methyl acid amide and N-ethyl acid amide; N-aryl acid amides for example, N-phenyl acid amide; N,N-dialkyl acid amides for example, N,N-diethyl acid amide and N-ethyl-N-methyl acid amide; and acid amides with imidazole, 4-substituted imidazole and triazopyrrolidone.

Exemplary suitable condensation products include products obtained by condensation with N-hydroxysuccinimide, N-hydroxyphthalimide, dimethylhydroxylamine, diethylhydroxylamine, 1-hydroxypiperidine and an oxime.

Exemplary suitable protecting groups of the protecting group-protected derivative at the carboxyl group include a dialkylsilyl group, trialkylsilyl group, benzhydryl group, and the like.

Examples of salts of the cephalosporanic acid represented by the formula (I) or its derivative include salts at the carboxyl group and salts at the amino group. Exemplary suitable salts at the carboxyl group include salts with an alkali metal such as sodium and potassium;

an alkaline earth metal such as calcium and magnesium; ammonium; a nitrogen-containing organic base such as triethylamine, diethylamine, pyridine, N-methylpiperidine, N-methylmorpholine, N,N-dimethylaniline and dicyclohexylamine. Exemplary suitable salts at the amino group include salts containing various acids, for example, inorganic acids such as hydrochloric acid and sulfuric acid; carboxylic acids such as oxalic acid, formic acid, and trichloroacetic acid and trifluoroacetic acid; and a sulfonic acids such as methanesulfonic acid, toluenesulfonic acid and naphthalenesulfonic acid.

When the carboxyl group of the cephalosporanic acid of the formula (I) is a free carboxyl group or a group derived therefrom exclusive of a salt, it is not changed. However, when the carboxyl group of the cephalosporanic acid of the formula (I) is in the form of a salt, the salt is sometimes changed to a free carboxylic acid during the reaction according to the type of the salt and the reaction conditions. For example, when the starting material is a sodium salt of the cephalosporanic acid of the formula (I), sodium is liberated from the carboxyl group during the reaction. Further, when the 7-positioned amino group of the cephalosporanic acid of the formula (I) or its derivative at the carboxyl group is in the form of a salt, the salt is sometimes changed to an amino group during the reaction according to the type of the salt and the reaction conditions. For example, when the starting material is a salt of acetic acid at the amino group of the cephalosporanic acid of the formula (I) or its derivative, the acetic acid may be liberated from the amino group during the reaction according to the reaction conditions.

In the method of the present invention, the first member functions as a catalyst.

Exemplary suitable halides of antimony, tin, iron, zinc and bismuth include antimony penta chloride, antimony pentabromide, stannic chloride, stannic bromide, ferric chloride, ferric bromide, zinc chloride, zinc bromide, zinc iodide, bismuth chloride and bismuth bromide. Exemplary suitable complexes of halides of antimony, tin, iron, zinc and bismuth include complexes with dialkyl ethers such as diethyl ether, di-n-propyl ether and di-n-butyl ether; complexes with amines such as ethylamine, n-propylamine, n-butylamine, triethanolamine and dimethylsulfoxide; complexes with fatty acids such as acetic acid and propionic acid; complexes with nitriles such as acetonitrile and propionitrile; complexes with carboxylic acid esters such as ethyl acetate; and complexes with phenols such as phenol.

The first member may be used alone or in combination. From the standpoint of the yield of the desired product, it is preferred to use at least two first members selected from the abovementioned group.

The above-mentioned first member may be used in a molar amount of from about 0.1 to about 50 times that of the starting material, namely the cephalosporanic acid represented by the formula (I) or its derivative at the carboxyl group, or a salt thereof.

Further, the first member may also be employed in combination with at least one second member selected from the group consisting of boron trifluoride and complexes of boron trifluoride.

Exemplary suitable complexes of boron trifluoride include complexes with alcohols such as methanol, ethanol, propanol, isopropanol and butanol; complexes with dialkyl ethers such as diethyl ether and di-n-butyl ether; complexes with amines such as ethylamine, n-propylamine and n-butylamine; complexes with fatty acids such as acetic acid and propionic acid; and complexes with phenols such as phenol.

The above-mentioned second member may be used in a molar amount of from about 0.1 to about 50 times that of the cephalosporanic acid represented by the formula (I) or its derivative, or a salt thereof.

From the standpoint of the yield of the desired product, it is preferred to use the first member in combination with the second member.

Exemplary suitable alcohols represented by the formula (III) include primary alcohols, secondary alcohols and tertiary alcohols Examples of suitable unsubstituted alcohols include methanol, ethanol, propanol, isopropanol and butanol Examples of suitable substituents for substituted alcohols include a halogen atom, an aryl group, an alcoxy group, an alkylthio group, a nitro group, a cyano group, an alkylamino group, a dialkylamino group, an acylamino group and an acyl group.

The alcohols as mentioned above may generally be used in a molar amount of from about 1 to about 30 times that of the starting material, namely the cephalosporanic acid represented by the formula (I) or its derivative at the carboxyl group, or a salt thereof, when at least one first member is used as a catalyst. When at least one first member is used in combination with at least one second member the alcohol may preferably be used in a molar amount of from about 1.5 to about 15 times, more preferably from about 2.0 to about 10 times that of the second member.

The process of the invention is carried out in a solvent. Suitable examplary solvents are those organic solvents which do not have an adverse effect on the reaction, for example, nitriles such as acetonitrile, propionitrile, benzonitrile and malonitrile; nitroalkanes such as nitromethane, nitroethane and nitropropane; carboxylic acids such as acetic acid, formic acid, propionic acid and trifluoroacetic acid, and esters thereof; alkyl ketones such as acetone, methyl ethyl ketone, methyl isobutyl ketone and acetophenone; halogenated alkanes such as dichloromethane, chloroform, dichloroethane, carbon tetrachloride; halogenated alkenes such as dichloroethylene and trichloroethylene; acid amides such as formamide, dimethylformamide and acetamide; ethers such as diethyl ether, diisopropyl ether, tetrahydrofuran and ethylene glycol dimethyl ether; aromatic hydrocarbons such as benzene, toluene, chlorobenzene and nitrobenzene; alkanes such as n-hexane and heptane; alicyclic compounds such as cyclohexane; sulfolane; and dimethyl sulfoxide. The above-mentioned organic solvents may be used alone or in combination. The organic solvent may be used in an amount of from about 0.1 to about 200 times by weight that of the starting material, namely the cephalosporanic acid of the formula (I) or its derivative at the carboxyl group, or a salt thereof. The above-mentioned alcohols which are to be reacted with the starting material, i.e., the cephalosporanic acid represented by the formula (I) or its derivative at the carboxyl group, or a salt of the cephalosporanic acid or the derivative may serve as a solvent. Further, the above-mentioned complexes of halides of antimony, tin, iron, zinc and bismuth may also serve as a solvent. Moreover, in the case where the complexes of boron trifluoride are used in combination with a halide compound selected from the group previously set forth, the complexes of boron trifluoride may also serve as a solvent. However, it is preferred from the yield of the desired compound that the above-mentioned organic solvent be additionally employed in an amount at least about 0.1 time that of the starting material.

The reaction temperature is not critical. Generally, the reaction may be conducted at a temperature of from about −20° C. to about 90° C. The reaction time is also not critical and, generally, the reaction is allowed to proceed until the reaction is completed. Although the reaction time varies according to the types and amounts of the starting materials, catalysts and solvent, and the reaction temperature, the reaction time may generally be from aobut 1 minute to about 80 hours.

It is preferred that the reaction be allowed to proceed substantially in the absence of water. Therefore, according to need, a dehydrating agent may be added to the reaction system. As the dehydrating agent, there may be employed, for example, phosphorus compounds such as phosphorus pentoxide, polyphosphate, phosphorus pentachloride, phosphorus trichloride and phosphorus oxichloride; organic silane derivatives such as N,O-bis-(trimethylsilyl)acetamide, trimethylsilylacetamide, trimethylchlorosilane and dimethyldichlorosilane; acid anhydrides such as acetic anhydride and trifluoroacetic anhydride; and inorganic desiccating agents such as anhydrous magnesium sulfate, anhydrous calcium chloride, anhydrous calcium sulfate and Molecular Sieves. In the case when the dehydrating agent is a phosporus compound, an organic silane derivative or an acid anhydride, the dehydrating agent may be employed in a molar amount of from about of from about 0.001 to about 5 times that of the starting material, namely a cephalosporanic acid represented by the formula (I) or its derivative, or a salt thereof. On the other hand, in the case when the dehydrating agent is an inorganic desiccating agent, the dehydrating agent may be employed in an amount of from about 0.01 to about 5 times by weight that of the starting material.

In the formula (II) above, $R_3$ represents an unsubstituted or substituted lower alkyl group. As used herein, the term "lower alkyl group" means an alkyl group having from 1 to 5 carbon atoms. Examples of suitable unsubstituted alkyl groups include methyl groups, ethyl groups, propyl groups, isopropyl groups and butyl groups. Examples of substituents of substituted alkyl groups include halogen atoms, aryl groups, alkoxy groups, alkylthio groups, nitro groups, cyano groups, alkylamino groups, dialkylamino groups, acylamino groups and acyl groups.

Exemplary suitable derivatives at the carboxyl group of the 3-alkoxymethyl-3-cephem-4-carboxylic acid represented by the formula (II) are those derivatives previously set forth with respect to the derivative at the carboxyl group of cephalosporanic acid represented by the formula (I).

Exemplary suitable salts of the 3-alkoxymethyl-3-cephem-4-carboxylic acid of the formula (II) or its derivative are those salts previously set forth with respect to the salt of the cephalosporanic acid of the formula (I) or its derivative.

After completion of the reaction, the thus prepared 3-alkoxymethyl-3-cephem-4-carboxylic acid of the formula (II) or its derivative at the carboxyl group, or a salt of the carboxylic acid or the derivative may be isolated from the reaction mixture by a customary method. For example, cold water may be added to the reaction mixture. If a precipitate is formed, the precipitate which is an impurity may be filtered off to obtain a filtrate, the pH of which may be adjusted to a pH value of from about 6 to about 8. If a precipitate is not formed, the reaction mixture may then be directly treated to adjust the pH to a value of from about to 6 to about 8. At a pH valve of from about 6 to about 8 impurities are precipitated. The precipitate is filtered off. The filtrate is then adjusted to a pH of from about 3 to 4 to precipitate the desired product. The precipitate is collected by filtration to obtain the desired product. Alternatively, the filtrate obtained by the above-mentioned pH adjustment to 6 to 8 and the subsequent filtration may be subjected to reversed phase adsorption chromatography before precipitating the desired product at pH 3 to 4.

Thus, the 3-alkoxymethyl-3-cephem-4-carboxylic acid of the formiula (II) or its derivative at the carboxyl group, or a salt of the carboxylic acid or the derivative is obtained.

The derivatives at the carboxyl group of the 3-alkoxymethyl-3-cephem-4-carboxylic acid of the formula (II), and the salts of the carboxylic acid and the derivatives may also be prepared from the 3-alkoxymethyl-3-cephem-4-carboxylic acid of the formula (II) by a customary method.

When the reaction product is the derivative at the carboxyl group of the 3-alkoxymethyl-3-cephem-4-carboxylic acid, the group derived from the carboxyl group may, if desired, be converted to a carboxyl group or a salt thereof by a customary method, for example, treatment with trifluoroacetic acid, hydrogen bromide, or hydrogen fluoride, and the like.

According to the process of the present invention, a 3-alkoxymethyl-3-cephem-4-carboxylic acid of the formula (II) or its derivative at the carboxyl group, or a salt of the carboxylic acid or the derivative can be prepared easily with high purity in high yield The above-mentioned carboxylic acid or the derivative, or a salt thereof is an important intermediate for producing various cephem antibiotics. Therefore, the present invention has an advantage that the intermediates useful for producing various cephem antibiotics can be easily prepared in high yield on a commercial scale.

The present invention will now be described in detail with reference to the following Examples, which are intended to be merely illustrative of the present invention.

In the following Examples, the yield of the desired product was calculated by the following formula:

$$\{A \approx (B \times D/C)\} \times 100 \, (\%)$$

wherein A is the amount (g) of the desired product, B is the amount (g) of the starting material, C is the molecular weight of the starting material and D is the molecular weight of the desired product.

EXAMPLE 1

To 10 ml of nitromethane were added 2.72 g of of 7-amino-cephalosporanic acid (hereinafter referred to as "7-ACA"), 9.63 g of zinc chloride and 0.71 g of methanol. The mixture was heated at 60° C. for 90 min to advance a reaction. After completion of the reaction, the reaction mixture was cooled to 5° C. To the reaction mixture were added 30 ml of water and 10 ml of methanol. Then, the mixture was adjusted to pH 7.8 with aqueous ammonia at a temperature of from −2° C. to 2° C. The resulting precipitate was filtered off, and then washed with water. The filtrate was combined with the washings. The resulting mixture was adjusted to pH 3.5 with 36 % hydrochloric acid to thereby form a precipitate. The precipitate was collected by filtration, and washed with 10 ml of cold water and, then, with 20 ml of cold methanol to obtain the desired product, namely 7-amino-3-methoxymethyl-3-cephem-4-carboxylic acid. The amount of the desired product was 0.98 g. The yield of the desired product was 40 %.

The molecular structure of the desired product was analysed by nuclear magnetic resonance (hereinafter referred to as "NMR") and infrared (hereinafter referred to as "IR") spectrophotometry. The results are as follows.

NMR (solvent: $CF_3COOD$)
Chemical shift [ppm]
3.63 (3H, s, $-CH_2OCH_3$)
3.77 (2H, s, $-CH_2-$ at the 2-position)
4.86 (2H, s, $-CH_2OCH_3$)
5.43 (2H, s, H at the 6-and 7-positions)
IR spectrum (Nujol method)
($cm^{-1}$)
3160 ($-NH_2$)
1800 ($>C=O$, $\beta$-lactum)
1620 ($-COOH$)
1100 ($-CH_2OCH_3$)

EXAMPLE 2

To 10 ml of nitromethane were added 2.72 g of 7-ACA, 11.2 g of ferric chloride and 2.1 g of methanol. The mixture was heated at 30° C. for 40 min while stirring to advance a reaction. After completion of the reaction, the reaction mixture was cooled to 5° C. To the reaction mixture was added 50 ml of water. Then, the mixture was adjusted to pH 1.0 with sodium bicarbonate and, then, further adjusted to pH 7.5 with sodium sulfide while cooling on ice. The resulting precipitate was filtered off, and then washed with water. The filtrate was combined with the washings. The resulting mixture was adjusted to pH 7 with 1N HCl and applied to a column packed with HP-20 (a packing material for reversed phase adsorption chromatography manufactured and sold by Mitsubishi Chemical Industries, Ltd., Japan). Then, the elution was conducted using water as an eluent, thereby to obtain an eluate. Then, the eluate was adjusted to pH 3.5 with 36 % hydrochloric acid to thereby form a precipitate. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.02 g. The yield of the desired product was 42 %.

The molecular structure of the desired product was analysed by NMR and IR spectrophotometry. The results were the same as those obtained in Example 1.

EXAMPLE 3

To 10 ml of sulfolane were added 2.72 g of 7-ACA, 9.0 g of zinc chloride and 1.40 g of methanol. The mixture was heated at 60° C. for 100 min to advance a reaction. After completion of the reaction, the reaction mixture was cooled to 5° C. To the reaction mixture were added 10 ml of water and 20 ml of methanol. Then, the mixture was adjusted to pH 7.7 with aqueous ammonia at a temperature of from −2° C. to 2° C. The resulting precipitate was filtered off, and then washed with water. The filtrate was combined with the washings. The resulting mixture was adjusted to pH 3.5 with 36 % hydrochloric acid to thereby form a precipitate. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.02 g. The yield of the desired product was 42 %.

The molecular structure of the desired product was analysed by NMR and IR spectrophotometry. The results were the same as those obtained in Example 1.

EXAMPLE 4

To 10 ml of carbon tetrachloride were added 2.72 g of 7-ACA, 15 g of antimony pentachloride and 1.40 g of methanol. The mixture was cooled at 10° C. for 80 min to advance a reaction. After completion of the reaction, the reaction mixture was cooled to 5° C. To the reaction mixture was added 150 ml of water. Then, the mixture was adjusted to pH 7.7 with sodium bicarbonate at a temperature of from 0° C. to 5° C. The resulting precipitate was filtered off, and then washed with water. The filtrate was combined with the washings. The resulting mixture was adjusted to pH 3.5 with 36 % hydrochloric acid, and then concentrated by evaporation under reduced pressure so that a precipitate was formed. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 0.61 g. The yield of the desired product was 25 %.

The molecular structure of the desired product was analysed by NMR and IR spectrophotometry. The results were the same as those obtained in Example 1.

EXAMPLE 5

To 10 ml of sulfolane were added 2.72 g of 7-ACA, 19 g of bismuth trichloride and 1.1 g of methanol. The mixture was heated at 60° C. for 35 min to advance a reaction. After completion of the reaction, the reaction mixture was cooled to 5° C. The resulting precipitate was filtered off. To the filtrate was added 30 ml of water while cooling on ice. Then, the filtrate was adjusted to pH 3.5 with sodium bicarbonate at a temperature of from 0° C. to 5° C., thereby to form a white crystalline precipitate. The resulting precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 0.76 g. The yield of the desired product was 31 %.

The molecular structure of the desired product was analysed by NMR and IR spectrophotometry. The results were the same as those obtained in Example 1.

EXAMPLE 6

To 10 ml of nitromethane were added 2.72 g of 7-ACA, 6 g of stannic chloride and 1.0 g of methanol The mixture was heated at 30° C. for 60 min while stirring to advance a reaction. After completion of the reaction, the reaction mixture was cooled to 5° C. To the reaction mixture was added 100 ml of water. Then, the mixture was adjusted to pH 8.0 with sodium bicarbonate at a temperature of from 0° C. to 5° C. The resulting precipitate was filtered off, and then washed with water. The filtrate was combined with the washings The resulting mixture was adjusted to pH 3.5 with 36 % hydrochloric acid, and then concentrated by evaporation under reduced pressure so that a precipitate was formed. The precipitate was collected by filtration, and washed with 10 ml of cold water and, then, with 5 ml of cold methanol to obtain the desired product, namely 7-amino-3-methoxymethyl-3-cephem-4-carboxylic acid. The amount of the desired product was 0.49 g. The yield of the desired product was 20 %.

The molecular structure of the desired product was analysed by NMR and IR spectrophotometry. The results were the same as those obtained in Example 1.

EXAMPLE 7

To 10 ml of nitromethane were added 2.72 g of 7-ACA, 8 g of zinc bromide and 0.9 g of methanol. The mixture was heated at 60° C. for 80 min to advance a reaction. After completion of the reaction, the reaction mixture was cooled to 5° C. To the reaction mixture were added 10 ml of water and 5 ml of methanol. Then, the mixture was adjusted to pH 7.5 with aqueous ammonia at a temperature of from 0° C. to 5° C. The resulting precipitate was filtered off, and then washed with water. The filtrate was combined with the washings. The resulting mixture was adjusted to pH 3.5 with 36 % hydrochloric acid to thereby form a precipitate. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 0.71 g. The yield of the desired product was 29 %.

The molecular structure of the desired product was analysed by NMR and IR spectrophotometry. The results were the same as those obtained in Example 1.

EXAMPLE 8

To 10 ml of nitromethane were added 2.72 g of 7-ACA, 3.0 g of methanol, 10.0 g of zinc chloride and 3.1 g of antimony pentachloride. The mixture was heated at 50° C. for 25 min to advance a reaction. After completion of the reaction, the reaction mixture was cooled to 5° C. To the reaction mixture was added 150 ml of water. Then, the mixture was adjusted to pH 7.5 with sodium bicarbonate at a temperature of from 0° C. to 5° C. The resulting precipitate was filtered off, and then washed with water. The filtrate was combined with the washings. To the resulting mixture was added 0.3 g of activated charcoal, and the mixture was stirred, followed by filtration. The resulting filtrate was adjusted to pH 3.5 with 36 % hydrochloric acid, and then concentrated by evaporation under reduced pressure so that a precipitate was formed. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.64 g. The yield of the desired product was 67 %.

The molecular structure of the desired product was analysed by NMR and IR spectrophotometry. The results were the same as those obtained in Example 1.

EXAMPLE 9

To 13 ml of sulfolane were added 2.72 g of 7-ACA, 3.5 g of methanol, 8.0 g of zinc chloride and 2.9 g of antimony pentachloride. The mixture was heated at 50° C. for 80 min while stirring to advance a reaction. After completion of the reaction, the reaction mixture was cooled to 5° C. To the reaction mixture was added 150 ml of water. Then, the mixture was adjusted to pH 7.5 with sodium bicarbonate at a temperature of from 0° C. to 5° C. The resulting precipitate was filtered off, and then washed with water. The filtrate was combined with the washings The resulting mixture was concentrated by evaporation under reduced pressure, and adjusted to pH 7 with 1N HCl. Then, the mixture was applied to a column packed with XAD-II (packing material for reversed phase adsorption chromatography manufactured and sold by Rohm and Haas Co., U.S.A.). Then, the elution was conducted using water as an eluent to obtain an eluate The eluate was adjusted to pH 3.5 with 36 % hydrochloric acid to thereby form a precipitate. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.73 g. The yield of the desired product was 71 %.

The molecular structure of the desired product was analysed by NMR and IR spectrophotometry. The results were the same as those obtained in Example 1.

EXAMPLE 10

To 10 ml of nitromethane were added 2.72 g of 7-ACA, 2.7 g of methanol, 5.0 g of zinc chloride and 4.0 g of ferric chloride. The mixture was heated at 50° C. for 30 min to advance a reaction. After completion of the reaction, the reaction mixture was cooled to 5° C. To the reaction mixture was added 150 ml of water. Then, the mixture was adjusted to pH 7.5 with sodium bicarbonate at a temperature of from 2° C. to 5° C. The resulting precipitate was filtered off, and then washed with water. The filtrate was combined with the washings. The resulting mixture was concentrated by evaporation under reduced pressure, and adjusted to pH 7 with 1N HCl. Then, the mixture was applied to the same column as used in Example 2. The elution was conducted using water as an eluent to obtain an eluate. The eluate was adjusted to pH 3.5 with 36 % hydrochloric acid to thereby form a precipitate. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.63 g. The yield of the desired product was 67 %.

The molecular structure of the desired product was analysed by NMR and IR spectrophotometry. The results were the same as those obtained in Example 1.

EXAMPLE 11

To 10 ml of nitromethane were added 2.72 g of 7-ACA, 2.2 g of methanol, 9.0 g of bismuth trichloride and 5.9 g of ferric chloride. The mixture was heated at 30° C. for 160 min to advance a reaction After completion of the reaction, the reaction mixture was cooled to 5° C. To the reaction mixture was added 50 ml of water. Then, the mixture was adjusted to pH 1 with sodium bicarbonate and, then, further adjusted to pH 7.5 with sodium sulfide while cooling on ice. The resulting precipitate was filtered off, and then washed with water. The filtrate was combined with the washings. The resulting mixture was adjusted to pH 3.5 with 36 % hydrochloric acid. To the mixture was added 50 ml of methanol, and the mixture was allowed to stand at 5° C. for 10 hours, thereby to form a precipitate. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.37 g. The yield of the desired product was 56 %.

The molecular structure of the desired product was analysed by NMR and IR spectrophotometry. The results were the same as those obtained in Example 1.

EXAMPLE 12

To 20 ml of carbon tetrachloride were added 2.72 g of 7-ACA, 2.6 g of methanol, 2.7 g of stannic chloride and 15 g of bismuth trichloride. The mixture was heated at 50° C. for 40 min to advance a reaction. After completion of the reaction, the reaction mixture was cooled to 5° C. The resulting precipitate was filtered off. To the filtrate was added 50 ml of water and, then, 0.3 g of activated carbon, and then the mixture was stirred, followed by filtration. The filtrate was adjusted to pH 3.5 with sodium bicarbonate, and concentrated by evaporation under reduced pressure, thereby to form a precipitate. The precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.29 g. The yield of the desired product was 53 %.

The molecular structure of the desired product was analysed by NMR and IR spectrophotometry. The results were the same as those obtained in Example 1.

EXAMPLE 13

To 15 ml of sulfolane were added 2.72 g of 7-ACA, 2.3 g of methanol, 2.8 g of antimony pentachloride and 12 g of bismuth trichloride. The mixture was heated at 50° C. for 40 min to advance a reaction. After completion of the reaction, the reaction mixture was cooled to 5° C. The resulting precipitate was filtered off To the filtrate was added 60 ml of water, and then the resulting mixture was stirred homogeneously. To the resulting solution was added 0.5 g of activated carbon, and then the mixture was stirred, followed by filtration. The filtrate was adjusted to pH 3.5 with sodium bicarbonate. To the resulting mixture was added 30 ml of methanol, thereby to form a white crystalline precipitate. The white crystalline precipitate was collected by filtration, and washed with 10 ml of cold water and, then, with 10 ml of cold methanol to obtain the desired product, namely 7-amino-3-methoxymethyl-3-cephem-4-carboxylic acid. The amount of the desired product was 1.29 g. The yield of the desired product was 53 %. .

The molecular structure of the desired product was analysed by NMR and IR spectrophotometry. The results were the same as those obtained in Example 1.

EXAMPLE 14

To 10 ml of nitromethane were added 2.72 g of 7-ACA, 5.0 g of zinc chloride, 4.0 g of stannic chloride and 2.0 g of methanol. The mixture was heated at 30° C. for 2.5 hours while stirring to advance a reaction. After completion of the reaction, the reaction mixture was cooled to 5° C. To the reaction mixture was added 60 ml of water. Then, to the mixture was added 0.2 g of activated carbon. The mixture was stirred, followed by filtration. The resulting filtrate was adjusted to pH 3.5 with sodium bicarbonate. The mixture was concentrated by evaporation under reduced pressure. The resulting crystalline precipitate was collected by filtration and sufficiently washed with 10 ml of cold water and, then, with 10 ml of cold methanol to obtain 1.46 g of the desired product, namely 7-amino-3-alkoxymethyl-3-cephem-4-carboxylic acid. The yield of the desired product was 60 %.

The molecular structure of the desired product was analysed by NMR and IR spectrophotometry. The results were the same as those obtained in Example 1.

EXAMPLE 15

To 15 ml of sulfolane were added 2.72 g of 7-ACA, 4.9 g of zinc chloride, 9.8 g of bismuth trichloride and 2.0 g of methanol. The mixture was heated at 60° C. for 40 min while stirring to advance a reaction. After completion of the reaction, the reaction mixture was cooled to 5° C. and the resulting precipitate was filtered off. To the filtrate was added 60 ml of water. To the resulting mixture was added 0.2 g of activated carbon. The mixture was stirred, followed by filtration. The resulting filtrate was adjusted to pH 3.4 with sodium bicarbonate. The mixture was concentrated by evaporation under reduced pressure so that the crystalline precipitate was formed. The crystalline precipitate was collected by filtration, and sufficiently washed with 10 ml of cold water and, then, with 10 ml of cold methanol to obtain 1.32 g of the desired product, namely 7-amino-3-alkoxymethyl-3-cephem-4-carboxylic acid. The yield of the desired product was 54%.

The molecular structure of the desired product was analysed by NMR and IR spectrophotometry. The results were the same as those obtained in Example 1.

EXAMPLE 16

To 10 ml of methylene chloride were added 2.72 g of 7-ACA, 5.0 g of ferric chloride, 2.70 g of stannic chloride and 2.2 g of methanol. The mixture was heated at 30° C. for 35 min to advance a reaction. After completion of the reaction, the reaction mixture was cooled to 5° C. To the reaction mixture was added 60 ml of water. Then, the mixture was adjusted to pH 7.5 with sodium bicarbonate at a temperature of from 2° C. to 5° C. The resulting precipitate was filtered off, and then washed with water. The filtrate was combined with the washings. The methylene chloride layer of the resulting mixture was removed. Then, the remaining layer was adjusted to pH 7 with 1N HCl and applied to the same column as used in Example 2. The elution was effected using water as an eluent. The eluate was adjusted to pH 3.5 with 36% hydrochloric acid to thereby form a precipitate. The precipitate was collected by filtration, and sufficiently washed with 10 ml of cold water and, then, with 10 ml of cold methanol to obtain 1.44 g of the desired product, namely 7-amino-3-alkoxymethyl-3-cephem-4-carboxylic acid. The yield of the desired product was 59%.

The molecular structure of the desired product was analysed by NMR and IR spectrophotometry. The results were the same as those obtained in Example 1.

EXAMPLE 17

To 15 ml of sulfolane were added 2.72 g of 7-ACA, 2.6 g of stannic chloride, 8.0 g of antimony pentachloride and and 1.9 g of methanol. The mixture was heated at 30° C. for 50 min while stirring to advance a reaction. After completion of the reaction, the reaction mixture was cooled to 5° C. To the reaction mixture was added 25 ml of water. To the mixture was added 0.3 g of activated carbon. The mixture was stirred, followed by filtration. The resulting filtrate was adjusted to pH 3.5 with sodium bicarbonate. The resulting solid formed in the mixture was collected by filtration and sufficiently washed with 10 ml of cold water and, then, 20 ml of cold methanol. The thus washed solid was put into a mixture of 20 ml of water and 5 ml methanol. The resulting mixture was adjusted to pH 8.0 with aqueous ammonia. To the mixture was added activated carbon. The mixture was stirred, followed by filtration. The resulting filtrate was adjusted to pH 3.5 with 36% hydrochloric acid to form a white crystalline precipitate. The crystalline precipitate was collected by filtration, and sufficiently washed with 15 ml of cold methanol to obtain 1.34 g of the desired product, namely 7-amino-3-alkoxymethyl-3-cephem-4-carboxylic acid. The yield of the desired product was 55%.

The molecular structure of the desired product was analysed by NMR and IR spectrophotometry. The results were the same as those obtained in Example 1.

EXAMPLE 18

To 15 ml of nitromethane were added 2.72 g of 7-ACA, 5.0 g of ferric chloride, 3.0 g of antimony pentachloride and 2.0 g of methanol. The mixture was heated at 30° C. for 45 min to advance a reaction. After completion of the reaction, the reaction mixture was cooled to 5° C. To the reaction mixture was added 60 ml of water. Then, the mixture was adjusted to pH 7.5 with sodium bicarbonate at a temperature of from 2° C. to 5° C. The resulting precipitate was filtered off, and then washed with water. The filtrate was combined with the washings. To the resulting mixture was added 0.3 g of activated carbon. The mixture was stirred, followed by filtration. The resulting filtrate was adjusted to pH 3.5 with 36% hydrochloric acid to thereby form a white crystalline precipitate. The white crystalline precipitate was collected by filtration, and sufficiently washed with 10 ml of cold water and, then, with 10 ml of cold methanol. Thus, 1.39 g of the desired product, namely 7-amino-3-alkoxymethyl-3-cephem-4-carboxylic acid was obtained. The yield of the desired product was 57%.

The molecular structure of the desired product was analysed by NMR and IR spectrophotometry. The results were the same as those obtained in Example 1.

EXAMPLE 19

To 15 ml of sulfolane were added 2.72 g of 7-ACA, 4.5 g of zinc chloride, 3.7 g of ferric chloride, 0.9 g of bismuth trichloride and 3.0 g of methanol. The mixture was heated at 50° C. for 35 min to advance a reaction. After completion of the reaction, the reaction mixture was cooled to 5° C. and the resulting precipitate was filtered off. To the filtrate was added 150 ml of water. Then, the mixture was adjusted to pH 7.5 with sodium bicarbonate at a temperature of from 2° C. to 5° C. The resulting precipitate was filtered off. The filtrate was concentrated under reduced presure and applied to the same column as used in Example 2 to effect elution using water as an eluent. The resulting eluate was adjusted to pH 3.5 with 36% hydrochloric acid to thereby form a precipitate. The precipitate was collected by filtration, and washed with 10 ml of cold water and, then with 10 ml of cold methanol to obtain 1.66 g of the desired product, namely 7-amino-3-alkoxymethyl-3-cephem-4-carboxylic acid. The yield of the desired product was 68%.

The molecular structure of the desired product was analysed by NMR and IR spectrophotometry. The results were the same as those obtained in Example 1.

EXAMPLE 20

To 5 ml of nitromethane were added 3.0 g of 7-ACA, 10.0 g of zinc chloride, 3.9 g of a complex of boron trifluoride with methanol (content of boron trifluoride: 51%) and 2.2 g of methanol. The mixture was heated at 60° C. for 30 min to advance a reaction. After completion of the reaction, the reaction mixture was cooled to 5° C. To the reaction mixture were added 30 ml of water and 5 ml of methanol. Then, the mixture was adjusted to pH 8.0 with 28% aqueous ammonia at a temperature of −5° C. The resulting precipitate was filtered off. The filtrate was adjusted to pH 3.5 with 36% hydrochloric acid to thereby form a precipitate. The precipitate was collected by filtration, and washed with 10 ml of cold water and, then, with 20 ml of cold methanol to obtain 1.75 g of the desired product, namely 7-amino-3-alkoxymethyl-3-cephem-4-carboxylic acid. The yield of the desired product was 65%.

The molecular structure of the desired product was analysed by NMR and IR spectrophotometry. The results were the same as those obtained in Example 1.

EXAMPLE 21

To 5 ml of nitromethane were added 3.0 g of 7-ACA, 10.0 g of zinc chloride, 6 g of a complex of boron trifluoride with methanol (content of boron trifluoride: 51%) and 3 g of methanol. The mixture was heated at 50° C. for 25 min to advance a reaction. After completion of the reaction, the reaction mixture was cooled to 5° C. Then, from the reaction mixture, nitromethane and methanol were removed by evaporation under reduced pressure. To the resultant mixture was added 10 ml of water. The thus obtained mixture was adjusted to pH 1.0 with sodium bicarbonate and, then, further adjusted to pH 7.5 with sodium sulfide while cooling on ice. The resulting precipitate was filtered off. The filtrate was adjusted to pH 7 with 1N HCl and applied to the same column as used in Example 2. The elution was conducted using water as an eluent. The resulting eluate was adjusted to pH 3.5 with 36% hydrochloric acid to thereby form a precipitate. The precipitate was collected by filtration, and washed with 10 ml of cold water and, then, with 10 ml of cold methanol to obtain 1.78 g of the desired product, namely 7-amino-3-alkoxymethyl-3-cephem-4-carboxylic acid. The yield of the desired product was 66%.

The molecular structure of the desired product was analysed by NMR and IR spectrophotometry. The results were the same as those obtained in Example 1.

EXAMPLE 22

To 10 ml of nitromethane were added 3.0 g of 7-ACA, 4.4 g of zinc chloride, 7.2 g of a complex of boron trifluoride with methanol (content of boron trifluoride: 51%) and 0.8 g of methanol. The mixture was heated at 50° C. for 60 min to advance a reaction. After completion of the reaction, the reaction mixture was cooled to 5° C. Then, from the reaction mixture, nitromethane and methanol were removed by evaporation under reduced pressure. To the resultant mixture was added 100 ml of water. The thus obtained mixture was adjusted to pH 7.0 with 1N HCl and applied to the same column as used in Example 2. The elution was conducted using water as an eluent. The eluate was adjusted to pH 3.5 with 36% hydrochloric acid to thereby form a precipitate. The precipitate was collected by filtration, and washed with 5 ml of cold water and, then, with 10 ml of cold methanol to obtain 1.45 g of the desired product, namely 7-amino-3-alkoxymethyl-3-cephem-4-carboxylic acid. The yield of the desired product was 53.9%.

The molecular structure of the desired product was analysed by NMR and IR spectrophotometry. The results were the same as those obtained in Example 1.

EXAMPLE 23

To 10 ml of acetonitrile were added 3.0 g of 7-ACA, 6.0 g of stannic chloride, 4.3 g of a complex of boron trifluoride with methanol, and 1.2 g of methanol. The mixture was heated at 55° C. for 40 min to advance a reaction. After completion of the reaction, the reaction mixture was cooled to 5° C. To the reaction mixture was added 100 ml of methanol. The thus obtained mixture was analyzed by high-performance liquid chromatography (HPLC) using as a packing material Cosmosil $_5C_{18}$ (manufactured and sold by Nakurai Chemical Ltd., Japan) and as an eluent a mixture of 5 parts by weight of acetonitrile, 95 parts by weight of water and 0.5 part by weight of ammonium acetate. As a result, it was found that 7-amino-3-methoxymethyl-3-cephem-4-carboxylic acid was produced with a yield of 59%.

EXAMPLE 24

To 10 ml of nitromethane were added 4.0 g of p-toluenesulfonate of methyl ester of 7-ACA, 4.0 g of zinc chloride, 7.0 g of a complex of boron trifluoride with methanol (content of boron trifluoride: 51%) and 1.2 g of methanol. The mixture was allowed to stand at 20° C. for 12 hours to advance a reaction. After completion of the reaction, the reaction mixture was cooled to 5° C. To the reaction mixture was added 100 ml of methanol. The thus obtained mixture was analyzed by HPLC in the same manner as in Example 24. As a result, it was found that methyl ester of 7-amino-3-methoxymethyl-3-cephem-4-carboxylic acid was produced with a yield of 72%.

EXAMPLE 25

To a mixed solvent consisting of 4 ml of nitromethane and 1 ml of tetrahydrofuran were added 3.0 g of 7-ACA, 9 g of ferric chloride, 12 g of a complex of boron trifluoride with methanol (content of boron trifluoride: 51%) and 3 g of methanol. The mixture was heated at 50° C. for 30 min to advance a reaction. After completion of the reaction, the reaction mixture was cooled to 5° C. To the reaction mixture was added 30 ml of water. The thus obtained mixture was adjusted to pH 1 with sodium bicarbonate and, then, further adjusted to pH 7.5 with sodium sulfide while cooling on ice. The resulting precipitate was filtered off. The filtrate was adjusted to pH 3.5 with 36% hydrochloric acid. Then, 100 ml of methanol was added to the filtrate and the resulting mixture was allowed to stand at 5° C. to form a precipitate. The precipitate was collected by filtration, and washed with 10 ml of cold water and, then, with 10 ml of cold methanol to obtain 1.70 g of the desired product, namely 7-amino-3-alkoxymethyl-3-cephem-4-carboxylic acid. The yield of the desired product was 63%.

The molecular structure of the desired product was analysed by NMR and IR spectrophotometry. The results were the same as those obtained in Example 1.

EXAMPLE 26

To 10 ml of nitromethane were added 3.0 g of 7-ACA, 10.0 g of zinc chloride and 3.9 g of a complex of boron trifluoride with methanol (boron trifluoride content: 51%). The mixture was heated at 60° C. for 20 min to advance a reaction. After completion of the reaction, the reaction mixture was cooled to 5° C. To the reaction mixture were added 30 ml of water and 5 ml of methanol. Then, the mixture was adjusted to pH 8.0 with 28% aqueous ammonia at a temperature of −5° C. The resulting precipitate was filtered off, and then washed with water. The filtrate was combined with the washings. The resulting mixture was adjusted to pH 3.5 with 36% hydrochloric acid to thereby form a precipitate. The precipitate was collected by filtration, and washed with 10 ml of cold water and, then, with 20 ml of cold methanol to obtain the desired product, namely 7-amino-3-methoxymethyl-3-cephem-4-carboxylic acid. The amount of the desired product was 1.4 g. The yield of the desired product was 52%.

The molecular structure of the desired product was analysed by NMR and IR spectrophotometry. The results were the same as those obtained in Example 1.

EXAMPLE 27

To 15 ml of sulfolane were added 3.0 g of 7-ACA, 5 g of antimony pentachloride and 3.0 g of a complex of boron trifluoride with methanol (boron trifluoride content: 51%) and 2.0 g of methanol. The mixture was heated at 60° C. for 40 min to advance a reaction. After completion of the reaction, the reaction mixture was cooled to 5° C. To the reaction mixture was added 100 ml of water. Then, the mixture was adjusted to pH 7.7 with sodium bicarbonate. The resulting precipitate was filtered off, and then washed with water. The filtrate was combined with the washings. The resulting mixture was adjusted to pH 3.5 with 36% hydrochloric acid, and concentrated under reduced pressure, thereby to form a white crystalline precipitate. The precipitate was collected by filtration, and washed with 10 ml of cold water and, then, with 20 ml of cold methanol to obtain the desired product, namely 7-amino-3-alkoxymethyl-3-cephem-4-carboxylic acid. The amount of the desired product was 1.53 g. The yield of the desired product was 57%.

The molecular structure of the desired product was analysed by NMR and IR spectrophotometry. The results were the same as those obtained in Example 1.

EXAMPLE 28

To 10 ml of carbon tetrachloride were added 3.0 g of 7-ACA, 15 g of bismuth trichloride and 3.0 g of a complex of boron trifluoride with methanol (boron trifluoride content: 51%) and 2.0 g of methanol. The mixture was heated at 60° C. for 90 min to advance a reaction. After completion of the reaction, the reaction mixture was cooled to 5° C. To the reaction mixture was added 50 ml of methanol. The resulting precipitate was filtered off, and then washed with water. The filtrate was combined with the washings. The resulting mixture was treated with 0.3 g of activated carbon and adjusted to pH 3.5 with aqueous sodium hydroxide to thereby form a precipitate. The precipitate was collected by filtration, and washed with 10 ml of cold water and, then, with 20 ml of cold methanol to obtain the desired product, namely 7-amino-3-alkoxymethyl-3-cephem-4-carboxylic acid. The amount of the desired product was 1.51 g. The yield of the desired product was 56%.

The molecular structure of the desired product was analysed by NMR and IR spectrophotometry. The results were the same as those obtained in Example 1.

EXAMPLE 29

To 10 ml of nitromethane were added 3.0 g of 7-ACA, 5.0 g of zinc chloride, 3.0 g of a complex of boron trifluoride with methanol (boron trifluoride content: 51%), 5.0 g of ferric chloride and 2.8 g of methanol. The mixture was heated at 50° C. for 40 min to advance a reaction. After completion of the reaction, the reaction mixture was cooled to 5° C. To the reaction mixture was added 50 ml of water. Then, the mixture was adjusted to pH 1 with sodium bicarbonate and then to pH 7.5 with sodium sulfide while cooling on ice. The resulting precipitate was filtered off, and then washed with water. The filtrate was combined with the washings. The resulting mixture was subjected to concentration under reduced pressure and then adjusted to pH 7 with 1N HCl. The mixture was applied to the same column as used in Example 2. The elution was conducted using water as an eluent. The resulting eluate was adjusted to pH 3.5 with 35% hydrochloric acid to thereby form a precipitate. The precipitate was collected by filtration, and washed with 10 ml of cold water and, then, with 10 ml of cold methanol to obtain the desired product, namely 7-amino-3-alkoxymethyl-3-cephem-4-carboxylic acid. The amount of the desired product was 1.72 g. The yield of the desired product was 64%.

The molecular structure of the desired product was analysed by NMR and IR spectrophotometry. The results were the same as those obtained in Example 1.

EXAMPLE 30

To 10 ml of nitromethane were added 3.0 g of 7-ACA, 10.0 g of zinc chloride, 4.4 g of a complex of boron trifluoride with diethylether and 2.8 g of methanol. The mixture was heated at 60° C. for 30 min to advance a reaction. After completion of the reaction, the reaction mixture was cooled to 5° C. To the reaction mixture were added 30 ml of water and 5 ml of methanol. Then, the mixture was adjusted to pH 8.0 with 25% aqueous ammonia at a temperature of −5° C. The resulting precipitate was filtered off, and then washed with 30 ml of water. The filtrate was combined with the washings. The resulting mixture was adjusted to pH 3.5 with 36% hydrochloric acid to thereby form a precipitate. Methanol, nitromethane and part of water in the mixture were distilled off under reduced pressure and the precipitate was collected by filtration, and washed with a mixture of 10 ml of cold water and 20 ml of cold methanol to obtain the desired product, namely 7-amino-3-alkoxymethyl-3-cephem-4-carboxylic acid. The amount of the desired product was 1.70 g. The yield of the desired product was 63.2%.

The molecular structure of the desired product was analysed by NMR and IR spectrophotometry. The results were the same as those obtained in Example 1.

EXAMPLE 31

To 8 ml of nitromethane were added 3.0 g of 7-ACA, 5.0 g of ferric chloride, 4.4 g of a complex of boron trifluoride with diethylether and 2.0 g of methanol. The mixture was heated at 50° C. for 15 min to advance a reaction. After completion of the reaction, the reaction mixture was cooled to 5 ° C. Nitromethane and methanol in the mixture were distilled off under reduced pressure. Then, to the resulting mixture was added 10 ml of water, and the mixture was adjusted to pH 1.0 with sodium bicarbonate. Then, the mixture was further adjusted to pH 7.5 with sodium sulfide while cooling on ice. The resulting precipitate was filtered off. The filtrate was adjusted to pH 7 with 1N HCl and applied to the same column as used in Example 2. The elution was conducted using water as an eluent. The resulting eluate was adjusted to pH 3.5 with 36% hydrochloric acid to thereby form a precipitate. The precipitate was collected by filtration, and washed with 10 ml of cold water and, then, with 10 ml of cold methanol to obtain the desired product, namely 7-amino-3-alkoxymethyl-3-cephem-4-carboxylic acid. The amount of the desired product was 1.70 g. The yield of the desired product was 63.2%.

The molecular structure of the desired product was analysed by NMR and IR spectrophotometry. The results were the same as those obtained in Example 1.

EXAMPLE 32

To 10 ml of nitromethane were added 3.5 g of 7-chloroacetamide-3-acetoxymethyl-3-cephem-4-carboxylic acid, n 9 g of zinc chloride and 0.9 g of methanol. The mixture was heated at 50° C. for 120 min to advance a reaction. After completion of the reaction, the reaction mixture was cooled to 5° C. To the reaction mixture was added 50 ml of cold water. The resulting mixture was subjected to extraction with 50 ml of ethyl acetate 3 times. The ethyl acetate layers were collected. The thus obtained ethyl acetate extract was washed with saline and dehydrated by means of anhydrous magnesium sulfate, followed by concentration under reduced pressure to obtain a solid product. To the product were successively added 30 ml of ethyl acetate and 0.3 g of activated carbon to effect decoloring. The resulting mixture was subjected to filtration, and to the resultant filtrate was added 1.3 g of dicyclohexylamine to precipitate a white crystalline substance. The mixture was cooled on ice and allowed to stand for 3 hours. The precipitate was collected by filtration, and washed with ethyl acetate to obtain the desired product, namely 7-chloroacetoamide-3-methoxymethyl-3-cephem-4-carboxylic acid dicyclohexylamine. The amount of the desired product was 1.96 g. The yield of the desired product was 39%.

The molecular structure of the desired product was analysed by NMR. The results are as follows.

NMR (solvent: CDCl$_3$)
Chemical shift [ppm]
0.7–2.4 (20H, m)
2.7–3.4 (2H, m)
3.28 (3H, s, —OCH$_3$)
3.42 (2H, s, CH$_2$ at the 2-position)
4.66 (2H, s, ClCH$_2$CO)
4.29 (2H, s, CH$_2$ at the 3-position)
4.96 (1H, d at the 6-position)
5.62 (1H, dd at the 7-position)
7.15 (1H, d, NH)

EXAMPLE 33

To 10 ml of nitromethane were added 10.0 g of zinc chloride and 5.8 g of methanol and then, to the mixture was introduced 2.0 g of gaseous boron trifluoride, while cooling on ice. To the mixture was added 3.0 g of 7-ACA and the resulting mixture was heated at 60° C. for 30 min to advance a reaction. After completion of the reaction, the reaction mixture was cooled to 5° C. To the reaction mixture were added 25 ml of water and 5 ml of methanol. Then, the mixture was adjusted to pH 7.8 with 28% aqueous ammonia at a temperature of −2° C. The resulting precipitate was filtered off, and then washed with water. The filtrate was combined with the washings. The resulting mixture was adjusted to pH 3.5 with 36% hydrochloric acid to thereby form a precipitate. The precipitate was collected by filtration, and washed with 10 ml of cold water and, then, with 20 ml of cold methanol to obtain the desired product, namely 7-amino-3-alkoxymethyl-3-cephem-4-carboxylic acid. The amount of the desired product was 1.72 g. The yield of the desired product was 63.9%.

The molecular structure of the desired product was analysed by NMR and IR spectrophotometry. The results were the same as those obtained in Example 1.

COMPARATIVE EXAMPLE 1

To 10 ml of carbon tetrachloride was added 3.9 g of a boron trifluoride-methanol complex. The mixture was heated at 60° C. for 30 min to advance a reaction. After completion of the reaction, the reaction mixture was cooled to 5° C. To the reaction mixture were added 30 ml of water and 5 ml of methanol. Then, the mixture was adjusted to pH 8.0 with 28% aqueous ammonia at a temperature of 0° C. The resulting precipitate was filtered off, and then washed with water. The filtrate was combined with the washings. The resulting mixture was adjusted to pH 3.5 with 36% hydrochloric acid to therebyl form a precipitate. The precipitate was collected by filtration, and washed with 10 ml of cold water and, then, with 20 ml of cold methanol to obtain the desired product, namely 7-amino-3-methoxymethyl-3-cephem-4-carboxylic acid. The amount of the desired product was 0.37 g. The yield of the desired product was as low as 13.8%.

The molecular structure of the desired product was analysed by NMR and IR spectrophotometry. The results were the same as those obtained in Example 1.

COMPARATIVE EXAMPLE 2

To 10 ml of carbon tetrachloride were added 2.72 g of 7-ACA, 4.3 g of a boron trifluoridediethylether complex, and 3.5 g of methanol. The mixture was heated at 60° C. for 35 min to advance a reaction. After completion of the reaction, the reaction mixture was cooled to 5° C. To the reaction mixture was added 20 ml of cold water. Then, the mixture was adjusted to pH 7.5 with 28% aqueous ammonia at a temperature of 5° C. The resulting precipitate was filtered off, and then washed with water. The filtrate was combined with the washings. The resulting mixture was applied to the same column as used in Example 2. The elution was conducted using water as an eluent. The resulting eluate was adjusted to pH 3.5 with 36% hydrochloric acid to hereby form a precipitate. The precipitate was collected by filtration, and washed with 5 ml of cold water and, then, with 5 ml of cold methanol to obtain the desired product, namely 7-amino-3-methoxymethyl-3-cephem-4-carboxylic acid. The amount of the desired product was 0.27 g. The yield of the desired product was as low as 11.1%.

The molecular structure of the desired product was analysed by NMR and IR spectrophotometry. The results were the same as those obtained in Example 1.

What is claimed is:

1. A process for preparing a 3-alkoxymethyl-3-cephem-4-carboxylic acid represented by the formula (II) or its derivative at the carboxyl group, or a pharmaceutically acceptable salt of said carboxylic acid or said derivative

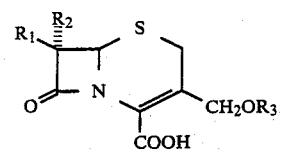

wherein $R_1$ represents an amino group, $R_2$ represents a hydrogen atom or a lower alkoxy group and $R_3$ represents a lower alkyl group unsubstituted or substituted with a halogen atom, an aryl group, an alkoxy group, an alkythio group, a nitro group, a cyano group, an alkylamino group, a dialkylamino group, an acylamino group and an acyl group, said derivative at the carboxyl group being selected from the group consisting of esters, amides and condensation products with N-hydroxysuccinimide, N-hydroxyphthalimide, dimethylhydroxylamine, diethylhydroxylamine, 1-hydroxypiperidine and an oxime, and protecting group-protected derivatives thereof, the process comprising the steps of:

reacting a cephalosporanic acid represented by the formula (I) or its derivative at the carboxyl group, or a pharmaceutically acceptable salt of said cephalosporanic acid or said derivative

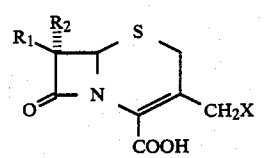

wherein $R_1$ and $R_2$ have the same meanings as defined above, and X represents an acetoxy group, said derivative at the carboxyl group being selected from the group consisting of esters, amides and condensation products with N-hydroxysuccinimide, N-hydroxyphthalimide, dimethylhydroxylamine, diethylhydroxylamine, 1-hydroxypiperidine and an oxime, and protecting group-protected derivatives thereof, with an alcohol represented by the formula (III):

$$R_3\text{—OH} \quad (III)$$

wherein $R_3$ has the same meaning as defined above, in the presence of one member selected from the group consisting of halides of antimony, iron, zinc and bismuth and complexes of said halides with dialkyl ethers, amines, fatty acids, nitriles, carboxylic acid esters and phenols.

2. The process according to claim 1, wherein said halides are selected from the group consisting of antimony pentachloride, antimony pentabromide, ferric chloride, ferric bromide, zinc chloride, zinc bromide, bismuth chloride and bismuth bromide.

3. The process according to claim 1, wherein said member is employed in a molar amount of from about 0.1 to about 50 times that of said cephalosporanic acid represented by the formula (I) or its derivative at the carboxyl group, or a pharmaceutically acceptable salt of said cephalosporanic acid or said derivative.

4. The process according to claim 1, wherein said alcohol is employed in a molar amount of from about 1 to about 30 times that of said cephalosporanic acid represented by the formula (I) or its derivative at the carboxyl group, or a pharmaceutically acceptable salt of said cephalosporanic acid or said derivative.

5. The process according to claim 1, wherein the reaction is conducted at a temperature of about −20° C. to about 90° C.

6. A process for preparing a 3-alkoxymethyl-3-cephem-4-carboxylic acid represented by the formula (II) or its derivative at the carboxyl group, or a pharmaceutically acceptable salt of said carboxylic acid or said derivative

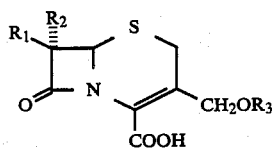 (II)

wherein $R_1$ represents an amino group, $R_2$ represents a hydrogen atom or a lower alkoxy group and $R_3$ represents a lower alkyl group unsubstituted or substituted with a halogen atom, an aryl group, an alkoxy group, an alkylthio group, a nitro group, a cyano group, an alkylamino group, a dialkylamino group, an acylamino group and an acyl group, said derivative at the carboxyl group being selected from the group consisting of esters, amides and condensation products with N-hydroxysuccinimide, N-hydroxyphthalimide, dimethylhydroxylamine, diethylhydroxylamine, 1-hydroxypiperidine and an oxime, and protecting group-protected derivatives thereof, the process comprising the steps of:

reacting a cephalosporanic acid represented by the formula (I) or its derivative at the carboxyl group, or a pharmaceutically acceptable salt of said cephalosporanic acid or said derivative

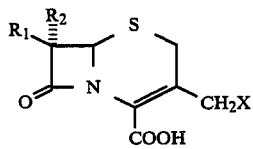 (I)

wherein $R_1$ and $R_2$ have the same meanings as defined above,
and X represents an acetoxy group, said derivative at the carboxyl group being selected from the group consisting of esters, amides and condensation products with N-hydroxysuccinimide, N-hydroxyphthalimide, dimethylhydroxylamine, diethylhydroxylamine, 1-hydroxypiperidine and an oxime, and protecting group-protected derivatives thereof,
with an alcohol represented by the formula (III):

 (III)

wherein $R_3$ has the same meaning as defined above,
in the presence of at least one first member selected from the group consisting of halides of antimony, tin, iron, zinc and bismuth and complexes of said halides with dimethyl ether, diethyl ether, dibutyl ether, methyl acetate ethyl acetate, acetic acid and phenol
in combination with at least one second member selected from the group consisting of boron trifluoride and complexes of boron trifluoride with dialkyl ethers, amines, fatty acids, phenols, and alcohols represented by the formula $R_4$—OH wherein $R_4$ represents a lower alkyl group.

7. The process according to claim 6, wherein said halides are selected from the group consisting of antimony pentachloride, antimony pentabromide, stannic chloride, stannic bromide, ferric chloride, ferric bromide, zinc chloride, zinc bromide, zinc iodide, bismuth chloride and bismuth bromide.

8. The process according to claim 6, wherein said first member is employed in a molar amount of from about 0.1 to about 50 times that of said cephalosporanic acid represented by the formula (I) or its derivative at the carboxyl group, or a pharmaceutically acceptable salt of said cephalosporanic acid or said derivative.

9. The process according to claim 6, wherein said second member is employed in a molar amount of from about 0.1 to about 50 times that of said cephalosporanic acid represented by the formula (I) or its derivative at the carboxyl group, or a pharmaceutically acceptable salt of said cephalosporanic acid or said derivative.

10. The process according to claim 6, wherein said alcohol is employed in a molar amount of from about 1 to about 30 times that of said cephalosporanic acid represented by the formula (I) or its derivative at the carboxyl group, or a pharmaceutically acceptable salt of said cephalosporanic acid or said derivative.

11. The process according to claim 10, wherein said alcohol is employed in a molar amount of from about 1.5 to about 15 times that of said second member.

12. The process according to claim 6, wherein the reaction is conducted at a temperature of about −20° C. to about 90° C.

13. The process for preparing a 3-alkoxymethyl-3-cephem-4-carboxylic acid represented by the formula (II) or its derivative at the carboxyl group, or a pharmaceutically acceptable salt of said carboxylic acid or said derivative

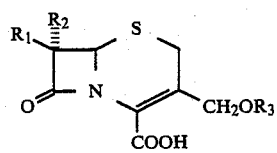 (II)

wherein $R_1$ represents an amino group, $R_2$ represents a hydrogen atom or a lower alkoxy group and $R_3$ represents a lower alkyl group unsubstituted or substituted with a halogen atom, an aryl group, an alkoxy group, an alkylthio group, a nitro group, a cyano group, an alkylamino group, a dialkylamino group, an acylamino group or an acyl group,
said derivative at the carboxyl group being selected from the group consisting of esters, amides and condensation products with N-hydroxysuccinimide, N-hydroxyphthalimide, dimethylhydroxylamine, diethylhydroxylamine, 1-hydroxypiperidine and an oxime, and protecting group-protected derivatives thereof, the process comprising:
reacting a cephalosporanic acid represented by the formula (I) or its derivative at the carboxyl group, or a pharmaceutically acceptable salt of said cephalosporanic acid or said derivative

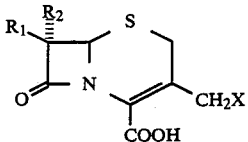

(I)

wherein $R_1$ and $R_2$ have the same meanings as defined above, an X represents an acetoxy group, said derivative at the carboxyl group being selected from the group consisting of esters, amides and condensation products with N-hydroxysuccinimide, N-hydroxyphthalimide, dimethylhydroxylamine, diethylhydroxylamine, 1-hydroxypiperidine and an oxime, and protecting group-protected derivatives thereof, with an alcohol represented by the formula (III):

$R_3—OH$ (III)

wherein $R_3$ has the same meaning as defined above, in the presence of at least two first members selected from the group consisting of halides of antimony, tin, iron, zinc and bismuth and complexes of said halides with dimethyl ether, diethyl ether, dibutyl ether, methyl acetate ethyl acetate, acetic acid and phenol.

14. The process according to claim 13, wherein said halides are selected from the group consisting of antimony pentachloride, antimony pentabromide, stannic chloride, stannic bromide, ferric chloride, ferric bromide, zinc chloride, zinc bromide, zinc iodide, bismuth chloride and bismuth bromide.

15. The process according to claim 13, wherein said first member is employed in a molar amount of from about 0.1 to about 50 times that of said cephalosporanic acid represented by the formula (I) or its derivative at the carboxyl group, or a pharmaceutically acceptable salt of said cephalosporanic acid or said derivative, said derivative at the carboxyl group being selected from the group consisting of esters, amides and condensation products with N-hydroxysuccinimide, N-hydroxyphthalimide, dimethylhydroxylamine, diethylhydroxylamine, 1-hydroxypiperidine and an oxime, and protecting group-protected derivatives thereof.

16. The process according to claim 13, wherein said alcohol is employed in a molar amount of from about 1 to about 30 times that of said cephalosporanic acid represented by the formula (I) or its derivative at the carboxyl group, or a pharmaceutically acceptable salt of said cephalosporanic acid or said derivative, said derivative at the carboxyl group being selected from the group consisting of esters, amides and condensation products with N-hydroxysuccinimide, N-hydroxyphthalimide, dimethylhydroxylamine, diethyhydroxylamine, 1-hydroxypiperidine and an oxime, and protecting group-protected derivatives thereof.

17. The process according to claim 13, wherein the reaction is conducted at a temperature of about $-20°$ C. to about $90°$ C.

* * * * *

UNITED STATES PATENT AND TRADEMARK OFFICE
CERTIFICATE OF CORRECTION

PATENT NO. : 4,902,793
DATED : February 20, 1990
INVENTOR(S) : Joji Nishikido et al.

It is certified that error appears in the above-identified patent and that said Letters Patent is hereby corrected as shown below:

Claim 1, col. 22, line 13: "alkythio" should be --alkylthio--.

Claim 3, col. 22, line 61: "0.1to" should be --0.1 to--.

Claim 13, col. 25, line 16: "groupprotected" should be --group-protected--.

Signed and Sealed this

Twenty-sixth Day of February, 1991

Attest:

HARRY F. MANBECK, JR.

*Attesting Officer*  *Commissioner of Patents and Trademarks*